United States Patent [19]

Page et al.

[11] Patent Number: 4,486,894
[45] Date of Patent: Dec. 4, 1984

[54] METHOD OF AND APPARATUS FOR SENSING THE ASH CONTENT OF COAL

[75] Inventors: Dennis Page, Gateshead; Edward J. Fox, Derby, both of England

[73] Assignee: Coal Industry (Patents) Limited, London, England

[21] Appl. No.: 339,512

[22] Filed: Jan. 15, 1982

Related U.S. Application Data

[63] Continuation-in-part of Ser. No. 165,016, Jul. 1, 1980, abandoned.

[30] Foreign Application Priority Data

Aug. 7, 1979 [GB] United Kingdom ................ 7927501

[51] Int. Cl.³ .................. G01N 23/203; G01N 23/223
[52] U.S. Cl. ...................................... 378/46; 378/88; 250/359.1; 250/255
[58] Field of Search .................. 250/493.1, 255, 359.1, 250/358.1; 378/46, 45, 88, 120

[56] References Cited

U.S. PATENT DOCUMENTS 3,404,275 1/1968 Martinelli .............................. 378/46
3,448,264 6/1969 Rhodes ................................. 378/46

FOREIGN PATENT DOCUMENTS 1065919 4/1967 United Kingdom .

OTHER PUBLICATIONS

Kneip, "Isotope Excited X-Ray Fluorescence", Anal. Chem., 44 (4), Dec. 1972, pp. 57A–68A.
Kawatra et al., "On-Line Measurements of Ash in Coal Slurries", Can. J. Spectrosc., 21 (2), Mar./Apr. 1976, pp. 58–60.

Primary Examiner—Alfred E. Smith
Assistant Examiner—Carolyn E. Fields
Attorney, Agent, or Firm—Stevens, Davis, Miller & Mosher

[57] ABSTRACT

The ash content of a granulor coal sample having a moisture content greater than 10% by weight is sensed by bombarding it with primary radiation comprising at least two spectrums of energies (46 KeV and 9–17 KeV) to cause radiative reactions in the coal, sensing the secondary radiation generated by the radiative reactions caused by one of the two spectrums of energies (46 KeV), sensing the secondary radiations at a characteristic fluorescent energy of at least one element (e.g. iron) in the coal sample, the characteristic fluorescent energy being excited by the other of the two spectrums of energies (9–17 KeV), and using the sensed secondary radiations to determine the ash content of the coal.

5 Claims, 2 Drawing Figures

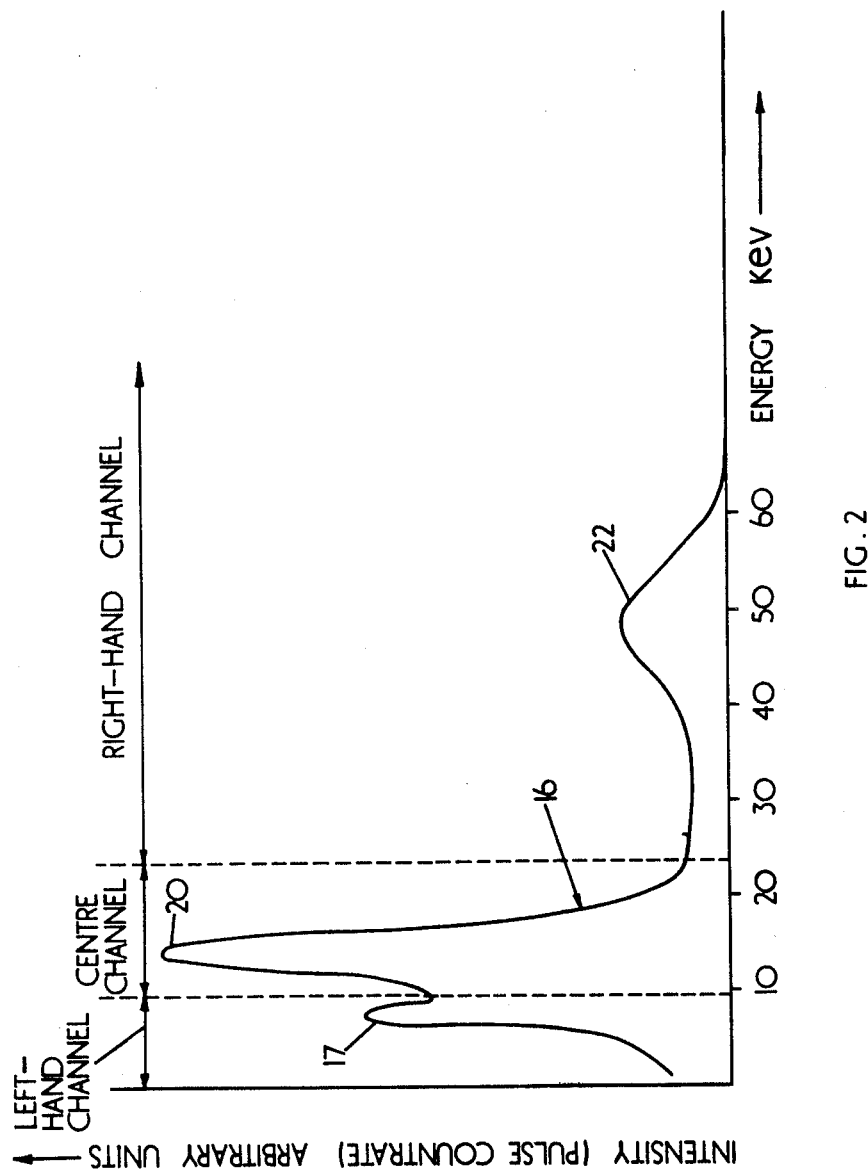

METHOD OF AND APPARATUS FOR SENSING THE ASH CONTENT OF COAL

This application is a continuation-in-part of U.S. application Ser. No. 165,016 filed July 1, 1980, now abandoned.

The invention relates to an improved method of and apparatus for sensing the ash content of coal.

This invention finds particular although not exclusive application in connection with monitoring and control of coal composition.

It is known to determine the ash content of coal by subjecting a sample of coal to radiation using a Plutonium 238 radioactive isotope source and Argon/Helium gas filled detector. The incident radiation from the Plutonium isotope has an energy of 15–17 KeV and it is backscattered or absorbed in relation to the absorption co-efficients of the elements present in the coal sample. The derived intensity or pulse count rate of the back-scattered radiation is detected and used to give an indication of the ash content in the coal sample.

However, in practice an incident radiation of 15 KeV results in a high sensitivity to variations in the concentration of iron which is a dominant element in the ash, the characteristic fluorescent radiation of iron being excited by the incident radiation. In order to try and reduce the effect of varying iron concentration it is necessary to detect the intensity or pulse count rate of the excited fluorescent iron radiation as well as the intensity or pulse countrate of the previously mentioned backscattered radiation and to combine the two intensities, suitably adjusting the excited fluorescent iron radiation intensity so that is just compensates for the decrease in backscattered intensity due to the presence of iron in the coal sample.

The intensity of back scattered radiation is affected by other factors including the free moisture content of the coal sample and the bulk density of the sample, this latter factor being principally dependent upon the particle size distribution in the sample and upon the moisture content. Where these two factors have been found to have a disturbing influence on the ash content determination using a Plutonium 238 isotope source it has been found that within the limits of a maximum particle size of 5 mm and a free moisture content of about 10% it is possible to apply a suitable correction, based upon the readings of a gamma radiation transmission density gauge, to compensate for changes in bulk density and in moisture content.

A further disturbing factor arises from the particle size in that above certain size limits, which are determined by the energy and hence the degree of penetration of the radiation into the coal and by the dimensions of the source to sample to detector radiation path length, variations in the surface contour of the bed of coal introduce unacceptably high errors into the ash content determination from back scattered intensity.

At a particle size limit of 5 mm problems can arise in the handling of the sample when the free moisture content approaches 10%, the problem increasing with increasing moisture content. Due to modern underground mining practices it now is becoming necessary to examine coal samples with higher than 10% free moisture content. One way of avoiding the handleability problems of coal samples with free moisture contents above 10% is to increase the maximum particle size but the relatively shallow penetration depth of incident radiation from a Plutonium 238 isotope renders it unsuitable for sensing the ash content of coal with a particle size greater than 5 mm.

It is known to sense the ash content of coal using higher energy incident radiation such as 60 KeV radiation from Americium 241 up to particle sizes of at least 60 mm. However this energy of radiation is still sensitive to the disturbing influence of variations in the iron content of the ash and furthermore is incapable of exciting the characteristic fluorescent radiation of iron to any significant degree which could allow for compensation. It is possible to generate an iron compensation signal by some other technique which is insensitive to particle size at this level, such as thermal neutron capture gamma interaction, but this involves the inconvenience and expense of setting up such a system.

A simpler process of exciting iron fluorescent radiation would be preferable but because of the low energy of this radiation the detected signal depends not only on the iron content of the coal but also on the surface contour of the bed which is itself dependent upon the particle size i.e. the iron fluorescence signal is to some extent particle size dependent. If the bed of coal is subjected to low energy radiation of an energy level not too far removed from the fluorescent energy then the back scattered radiation, in addition to its dependence upon ash content will also be sensitive to particle size to a similar degree to the fluorescent radiation. Comparison of this back scattered signal with that from higher energy radiation which is not sensitive to particle size provides an assessment of the particle size which may then be applied as a correction to the iron fluorescent signal.

An object of the present invention is to provide an improved method for sensing the ash content of the coal samples having high moisture content and large particle size. The present invention also provides apparatus for carrying out the improved method.

According to a first aspect of the present invention, a method of sensing ash in a coal sample comprises the steps of:

bombarding the coal sample with radiation from a single nucleonic source which emits primary radiation in at least two spectrums of energy, the first spectrum causing the coal sample to emit a first spectrum of secondary radiation, and the second spectrum causing the coal sample to emit a second spectrum of secondary radiation and to emit fluorescent radiation characteristic of iron from iron atoms in the coal sample;

sensing the first and second spectrums of secondary radiation and the characteristic iron fluorescent radiation, and determining from the sensed radiations the ash content of the coal sample.

Conveniently the first spectrum of primary radiation does not substantially excite the characteristic iron fluorescent radiation.

Preferably, the ash content of the coal sample is determined according to the equation:

$$\text{Ash content} \ \alpha k(I_1 + f_2 Fe + f_3 I_2),$$

wherein

Ash content = %w/w ash in the coal sample;
$I_1$ = sensed first spectrum of secondary radiation;
$I_2$ = sensed second spectrum of secondary radiation;

Fe = sensed characteristic iron fluorescent radiation; and k, $f_2$ and $f_3$ = constants.

According to a second aspect of the present invention, apparatus for sensing ash in a coal sample comprises:

a single nucleonic source for arrangement to bombard the coal sample with primary radiation, the nucleonic source emitting at least two spectrums of primary radiation, such that, in use, the first spectrum causes the coal sample to emit a first spectrum of secondary radiation and the second spectrum causes the coal sample to emit a second spectrum of secondary radiation and to emit fluorescent radiation characterstic of iron from iron atoms in the coal sample;

sensor means for sensing the spectrums of secondary radiation and the characterstic fluorescent iron radiation and for deriving electrical signals indicative of the sensed radiations; and an electrical circuit for processing the derived electrical signals to give an indication of the ash content of the coal sample.

Preferably, the single nucleonic source is a lead-210 source which emits gamma rays at an energy of about 46 KeV and readjustment X-rays from bismuth in the range 9 to 17 KeV.

Conveniently, the electrical circuit includes a microprocessor.

The invention will now be described, by way of example only, with reference to the accompanying drawings, in which:

FIG. 2 is a graph showing radioactivity.

FIG. 1 shows the apparatus for sensing the ash content of a coal sample comprising, for example, broken coal, ash and moisture. Typically the ash contains elements such as iron, aluminium, silicon, chlorine, titanium, potassium, calcium and sulphur.

Figure 1:
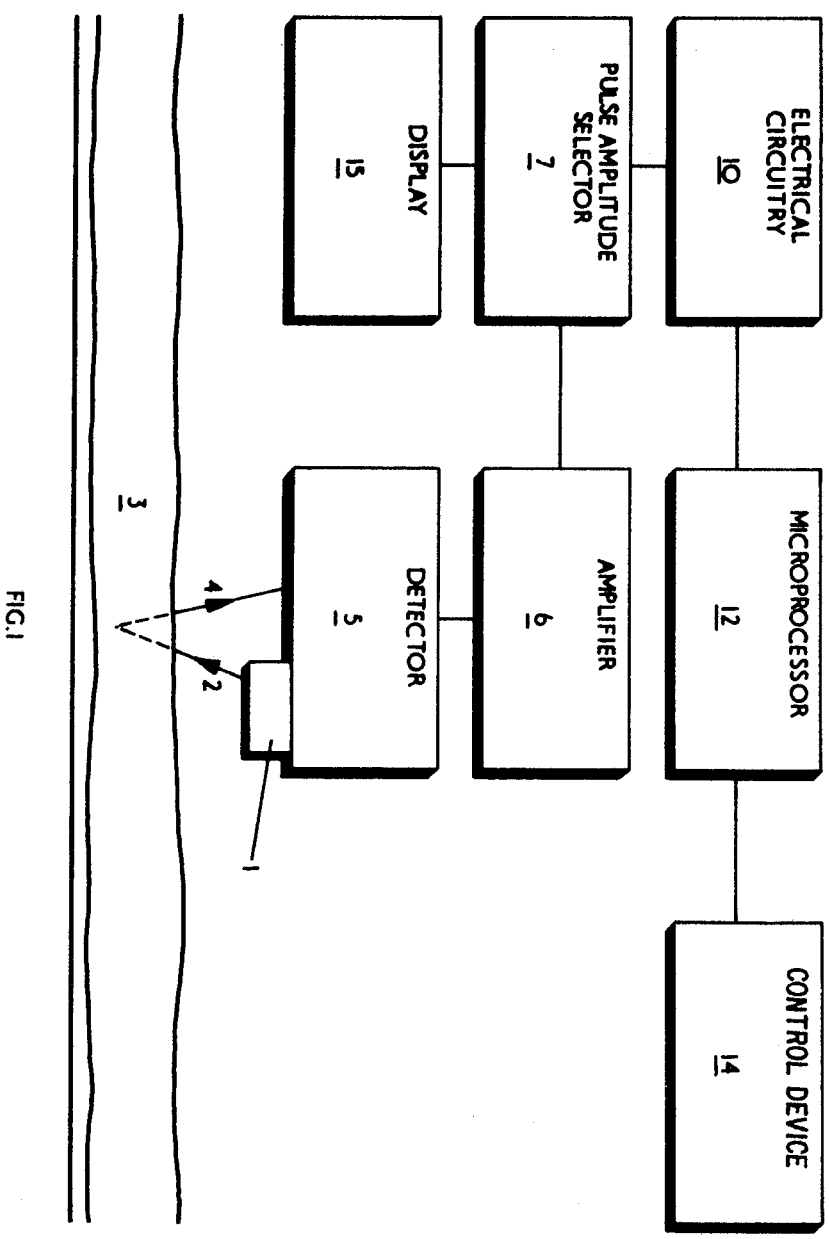
FIG. 1 is a block diagram of apparatus for sensing the ash content of coal sample.

In FIG. 1 a primary radiation source such as lead 210 is indicated at 1. The lead 210 source produces a first spectrum of electromagnetic radiation comprising a γ-emission of energies around 46 KeV and a second spectrum as a band of readjustment X-rays of energies 9-17 KeV, ie the Lead-210 source produces at least two spectrums of energies of primary radiation. The source 1 is arranged so that a beam 2 of primary radiation bombards a sample of coal 3 contained in a compacted layer formed on a moving deck. The beam 2 of primary radiation comprising the two spectrums of energies causes radiative reactions in the coal sample which generate associated spectrums of energies of secondary radiation, which are emitted from the coal sample as a beam 4 and which will be described later with reference to FIG. 2.

The intensity or pulse count rate of secondary radiation is detected by a detector 5, for example, a Xenon gas-filled proportional counter or a semiconductor detector or possibly two separate detector units, for example, a proportional counter for sensing the low energy radiation and a scintillation detector unit for sensing the higher energy radiation. The detector 5 is adapted to derive signals indicative of the intensity or pulse count rate. The signals are amplified by an amplifier 6 before being fed to a pulse amplitude selector 7 which selects only signals arising in desired parts of the full secondary radiation spectrum thereby separating the full spectrum into appropriate channels for further processing. Operation of the pulse selector is multiplexed so that more than one desired part of the full secondary spectrum can be selected.

The output signals from the selector 7 are fed to electrical circuitry 10 for conversion to a form suitable for use in a microprocessor 12 which is connected to a control device 14 such as speed regulators for controlling transport and bunkering of coal feeders feeding coal from which the sample was taken. A display 15 is provided for displaying the ash content or other signal arising in the circuitry.

FIG. 2, to which reference is now made, is a graph showing a typical secondary spectrum derived by interactions in the coal sample as sensed by the proportional counter of the detector 5. The graph shows intensity or pulse count rate of the secondary radiation plotted on the ordinate and energy on the abscissa. The resultant curve or full spectrum of energies over the depicted energies is indicated at 16. The graph shows the spectrum of energies divided into three channels. In the left hand channel there is shown the secondary radiation at the characteristic fluorescent intensity peak 17 which is derived from K-Shell transitions in iron, the characteristic fluorescent energy being excited by the band of readjustment X-rays of energies 9-17 KeV, ie by the primary radiation from bismuth L-Shell X-rays emitted from the lead-210 isotope source. The 46 KeV radiation does not excite iron fluorescence radiation to any significant extent and, therefore, cannot be employed as a means of compensation for iron fluorescence radiation. The intensity of the secondary radiation in the left hand channel is equivalent to the term Fe in the equation given above.

The central channel shows the secondary radiation intensity or pulse count rate 20 generated by the radiative reactions caused by the band of readjustment X-rays of energies 9-17 KeV, ie caused by the primary radiation from the bismuth L-Shell X-rays emitted from the lead-210 isotope source. The intensity of the secondary radiation in the central channel is equivalent to the term $I_2$ in the equation above, but is referred to below as Bi as it is caused by primary radiation from the bismuth.

The right hand channel shows the secondary radiation intensity or pulse count rate 22 generated by the radiative reactions caused by the γ-emission energies around 46 KeV emitted by the lead-isotope source.

The intensity of the secondary radiation in the right hand channel is equivalent to the term $I_1$ in the equation above, but is referred to below as Pbγ as it is caused by primary gamma radiation from the lead-210 source.

Thus, the detector 5 senses the full secondary radiation spectrum of energies and derives signals indicative of the sensed intensity or pulse count rate which are amplified by the amplifier 6 before being fed to the pulse amplitude selector 7 which as previously mentioned separates the full spectrum into appropriate channels. The selected output signals from the selector 7 are fed to electrical circuitry 10 for conversion to a form suitable for use in the microprocessor 12 which in turn suitably actuates the control device 14 to adjust the coal feeders feeding the coal from which the sample was taken. Any necessary adjustment is made such that the ash content of the coal feed is maintained at a desired level or within a preselected range.

In a typical arrangement the selector 7 is set such that the selected output signals are those associated with the three channels of FIG. 2 respectively. In this case the microprocessor 12 may determine the ash content by combining the intensity or pulse count rate of the backscattered radiation cause by the γ-emission of the energies around 46 KeV with the intensity or pulse count rate of the backscattered radiation caused by the band of readjustment X-rays of energies 9-17 KeV and with the intensity or pulse count rate of the excited fluorescent iron radiation, the latter two intensities being suitably adjusted.

In a typical arrangement the microprocessor determines the ash content of the coal sample using the equation:

Ash Content $\alpha K(Pb\gamma + f_2Fe + f_3Bi)$ where:
Ash Content = % Ash content of Coal in Sample;
Pbγ = sensed secondary radiation intensity or pulse Count rate caused by Lead factor of the Lead-210 isotope source (equivalent to $I_1$);
Fe = sensed secondary radiation intensity or pulse count rate of the excited fluorescent iron radiation;
Bi = sensed secondary radiation intensity or pulse count rate caused by Bismuth factor of the Lead-210 isotope source (equivalent to $I_2$); and
$f_2$ and $f_3$ = compensating constants.

In other examples it may be found that in order to obtain a more accurate determination of the ash content, a formula including a term defining a ratio of Sensed Iron Count rate to the Sensed Bismuth Count rate should be used. In other examples where the ash content to backscatter relationship is not linear over wide ash content ranges a more accurate ash content determination may be obtained by introducing a second order terms for at least a portion of the sensed secondary radiation In each example the appropriate formula is determined by experience and/or trial.

The primary radiation from the lead-210 source has a relatively high penetrating depth into coal. Consequently, with the present invention it is possible to sample coal of relatively large top size, for example, coal having a top size of around 5 cm. Therefore, using the present invention is it possible to sense and determine the ash content of coal samples have relatively high free moisture content, for example, it is possible to determine the ash content of coal having over 10% of free moisture.

In other embodiments of the present invention the electronic channel separation may be replaced or augmented by a mechanical filtration of the secondary arrangement which preferably absorbs the lower energies. Such an arrangement would tend to avoid the difficulties of accurate electronic setting and holding of the required channels. However, it would tend to introduce problems as, for example, a separate detector would be required for each channel measurement.

We claim:

1. A method of sensing the ash in a granular coal sample which sample has a coal particle size of up to 5 cm. and a moisture content greater than 10% by weight, comprising the steps of:
   bombarding the coal sample with radiation from a single nucleonic source which emits primary radiation in at least two spectrums of energy at around 46 KeV and around 13 KeV, the first spectrum around 46 KeV causing the coal sample to emit a first spectrum of secondary radiation, and the second spectrum around 13 KeV causing the coal sample to emit a second spectrum of secondary radiation and to emit fluorescent radiation characteristic of iron from iron atoms in the coal sample;
   sensing the first and second spectrums of secondary radiation and the characteristic iron fluorescent radiation; and
   determining from the sensed radiations the ash content of the coal sample.

2. A method according to claim 1, wherein the first spectrum of primary radiation does not substantially excite the characteristic iron fluorescent.

3. A method according to claim 1, wherein the ash content of the coal sample is determined according to the relationship:

Ash content $\alpha k(I_1 + F_2Fe + F_3I_2)$ where;
ash content = % W/W ash in the coal sample;
$I_1$ = sensed first spectrum of secondary radiation;
Fe = sensed characteristic iron fluorescent radiation;
$I_2$ = sensed second spectrum of secondary radiation; and
k, $F_2$ and $F_3$ = constants.

4. Apparatus for sensing ash in a granular coal sample, which sample has a coal particle size of up to 5 cm. and a moisture content greater than 10% by weight, comprising:
   a lead 210 source arranged to bombard the coal sample with primary radiation, the lead 210 source emitting at least two spectrums of primary radiation at around 46 KeV and around 13 KeV, such that in use the first spectrum around 46 KeV causes the coal sample to emit a first spectrum of secondary radiation and the second spectrum around 13 KeV causes the coal sample to emit a second spectrum of secondary radiation and to emit fluorescent radiation characteristic of iron from iron atoms in the coal sample;
   sensor means for sensing the spectrums of secondary radiation and the characteristic fluorescent iron radiation and for deriving electrical signals to give an indication of the ash content of the coal sample.

5. Apparatus according to claim 4, wherein the electrical circuit includes a microprocessor.

* * * * *